(12) United States Patent
Pertile

(10) Patent No.: US 8,741,961 B2
(45) Date of Patent: Jun. 3, 2014

(54) USE OF PARGYLINE FOR THE TREATMENT OF HAIR FOLLICLES

(75) Inventor: Paolo Pertile, San Pietro Viminario (IT)

(73) Assignee: Cutech S.r.l., Padua (IT)

( * ) Notice: Subject to any disclaimer, the term of this patent is extended or adjusted under 35 U.S.C. 154(b) by 451 days.

(21) Appl. No.: 12/231,385

(22) Filed: Sep. 2, 2008

(65) Prior Publication Data

US 2009/0069439 A1    Mar. 12, 2009

(30) Foreign Application Priority Data

Sep. 7, 2007 (EP) .................................. 07017594

(51) Int. Cl.
*A01N 33/02* (2006.01)
*A61K 31/135* (2006.01)
*A61K 9/48* (2006.01)

(52) U.S. Cl.
USPC .......................................... 514/646; 424/451

(58) Field of Classification Search
USPC ........................................................ 514/880
See application file for complete search history.

(56) References Cited

U.S. PATENT DOCUMENTS

| | | | |
|---|---|---|---|
| 3,257,277 A | 6/1966 | Hwang et al. | |
| 5,444,095 A * | 8/1995 | Tatton et al. | 514/654 |
| 6,277,892 B1 | 8/2001 | Deckner et al. | |
| 6,344,448 B1 * | 2/2002 | Brown | 514/179 |
| 6,818,296 B1 * | 11/2004 | Garces Garces et al. | 428/402.2 |
| 2004/0241220 A1 | 12/2004 | DiSanto | |

FOREIGN PATENT DOCUMENTS

| | | |
|---|---|---|
| EP | 0 351 897 | 1/1990 |
| GB | 955949 | 4/1964 |
| GB | 1578 852 | 11/1980 |
| GB | 1578852 | 11/1980 |
| WO | 93/07903 A1 | 4/1993 |

OTHER PUBLICATIONS

Nigam et al., "Techniques for Preparing Hydrogel Membrane Capsules", 1988, Biotechnology Techniques, vol. 2, No. 4, pp. 271-276.*
Malorni, W et al., "Protection against apoptosis by monoamine oxidase A inhibitors," FEBS Lett. 426, pp. 155-159 (1998).
Toninello A et al., "Amine oxidases in apoptosis and cancer," Biochim. Biophys. Acta 1765; pp. 1-13 (2006).
De Marchi, U et al., "L-Deprenyl as an inhibitor of menadione-induced permeability transition in liver mitochondria," Biochem. Pharmacol. 66(9):17, pp. 49-54 (2003).
Sullivan, G et al., "Hair loss associated with moclobemide use", Human Psychopharmacology 1997 United Kingdom, vol. 12, No. 1, 1997, pp. 81-82.
Tabamo R.E. et al., "Alopecia induced by dopamine agonists, " Database accession No. EMB-2002095740 & Neurology Mar. 12, 2002 United States, vol. 58, No. 5. pp. 829-830.
Gautam M. "Alopecia due to psychotropic medications" Database accession No. EMB-1999193283 & Annals of Pharmacotherapy 1999 United States, vol. 33, No. 5, 1999, pp. 631-637.
Papadopoulos, A.J. et al.: "Trichotillomania," database accession No. EMB-20032288689 & International Journal of Dermatology May 1, 2003 United Kingdom vol. 42, No. 5, pp. 330-334.

* cited by examiner

*Primary Examiner* — Gina C Justice
*Assistant Examiner* — Michael B Pallay
(74) *Attorney, Agent, or Firm* — Dilworth & Barrese, LLP

(57) ABSTRACT

Use of Pargyline for the production of a medicament for influencing the metabolism of hair follicles and the modulation of their vital cycle.

29 Claims, No Drawings

USE OF PARGYLINE FOR THE TREATMENT OF HAIR FOLLICLES

FIELD OF THE INVENTION

The present invention relates to the use of Pargyline for the production of medicaments for the treatment of various diseases associated with disorders of hair follicles and/or cosmetic compositions, as well as a process for curing said diseases and disorders by using said compound.

BACKGROUND OF THE INVENTION

It is well known from the state of the art that each hair follicle undergoes repeated cycles characterized by three stages: growth (anagen), involution (catagen), and resting phase (telogen). During anagen, the longest phase of the cycle, the follicle reaches its maximum growth potential. The matrix cells actively proliferate giving origin to the main anatomical structures of the follicle: the internal root sheath and the hair shaft (composed by cuticula, cortex and medulla). During catagen much of the follicle undergoes programmed cell death that causes the disassembling of the hair bulb (the hair shaft factory) and the reduction of the hair follicle size. At the end of this phase the hair follicle enters telogen, during which the proliferative and biochemical activity of the organ reaches its lowest level.

The duration of the various stages of the life cycle of the hair follicle varies with the age of the individual and the region of the body where the hair grows. For example, whereas in the scalp region anagen lasts from two to eight years, compared with a period of a few weeks for the catagen stage and a few months for the telogen stage, in the eyebrow region the anagen stage lasts for only a few months. This time ratio also determines the percentage of hair follicles which are present, on average, in the various stages of the cycle, for each region of the body. The durations of the various stages of the cycle, as well as the transition between one stage and another, are regulated by complex biological interactions, the mechanisms of which are not entirely clear, between the various parts of the hair follicle and between the follicle and the surrounding epithelial environment. It is, however, known that these stages are affected by many endogenous and exogenous factors which act, directly or indirectly, on the hair follicle to lengthen or shorten the duration of each individual stage.

Many attempts have been made to identify factors that cause an early entry into the catagen phase or disorders of the hair follicle, and to provide actives to fight these symptoms, however, with little success so far. It is believed that an active that promotes hair growth and, particularly, fights truly successfully against hair loss, would double the existing market for men's hair care products world-wide.

The present invention relates to the problems explained above and, more particularly, it aims to propose a treatment to fight hair loss based on increasing the anagen period of the hair follicles cycle and, as a consequence, on retarding the entry into catagen. At the same time, the growth of the hair follicles should be stimulated along with an increase of the number of cells in the proliferative stage. Finally, the new compositions should avoid any increase in cell apoptosis.

The invention discloses novel biological activities of Pargyline, yet known as Monoamine Oxydase Inhibitor (MAOI). As discussed below in details, the MAOIs are traditionally exploited for their activity on MAOs located in different tissues of the human body, but no activity on hair follicle metabolism has been disclosed so far.

In this context, attention is drawn to US 2004/0241220 A1 (DiSanto), dealing with the use of the S(+) enantiomer of desmethylselegiline (N-methyl-N-(prop-2-yinyl)-2-aminophenylpropane) ["S(+)DMS"]

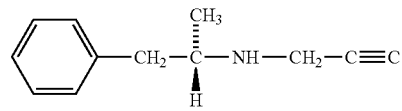

for the treatment of Selegiline-responsive diseases in general and for the treatment of narcolepsy in particular. The specification [0005]-[0006] refers to the fact that Selegilines are well-known MAO inhibitors. In section [0030], the "Selegiline responsive diseases", which are related to neuronal disorders or trauma, are listed and, among these, also alopecia is mentioned. However, the considered application bases all disclosed novel effects on the Selegiline's activity on the nervous system.

In the present invention, on the contrary, the disclosed effects have been studied on hair follicles excised and maintained in organ culture in order to prevent influences related to the metabolism of other tissues or modulated via the general metabolism of the donor. The described direct effects on the metabolic processes of the isolated hair follicle do not find any reference in the prior art.

DETAILED DESCRIPTION OF THE INVENTION

The present invention refers to the use of Pargyline for the production of a medicament to influence the metabolism of hair follicles and the modulation of their vital cycle.

Surprisingly it has been observed that among the known MAO inhibitors, Pargyline has a strong effect on cell proliferation and increases hair follicle growth. At the same time Pargyline delays the decline of the catagen phase and prolongs the anagen phase, during which the growth of the hair follicles can take place. Finally, the numbers of proliferative cells are significantly increased while cell apoptosis remains at the same level. The conclusion of these results, which are supported by detailed experimental data, is that Pargyline represents a rather effective active agent to treat many kinds of diseases that are associated with disorders of hair follicles including those types of skin diseases which are mediated by disorders or diseases of hair follicles.

Pargyline

MAO inhibitors, to which Pargyline counts, represent a type of antidepressants and are well known for the treatment of mental depression. Like other antidepressant drugs, MAO inhibitors help reduce the extreme sadness, hopelessness, and lack of interest in life that are typical in people with depression. MAO inhibitors are reported to be especially useful in treating people whose depression is combined with other problems, such as anxiety, panic attacks, phobias, or the desire to sleep too much. Discovered in the 1950s, MAO inhibitors work by correcting chemical imbalances in the brain. Normally, natural chemicals called neurotransmitters carry signals from one brain cell to another. Some neurotransmitters, such as serotonin, dopamine and norepinephrine, play important roles in controlling the mood. Certain proteins, so-called monoamine oxidases, are involved in the modulation of the nervous signal by interrupting the nervous stimulus via oxidative deamination of neurotransmitters. The unbalanced regulation of this reaction can produce severe psychic disorders, and some therapies are based on the properties of MAO inhibitors, which work by blocking said enzymes and are therefore protecting the neurotransmitters.

Scientific literature attests that MAOs are involved in other important metabolic pathways as well, with different implications related to the body tissue considered. Important effects of MAO's activity in mitochondria have been highlighted, for example, in the control of cell apoptosis, suggesting the possibility to prevent this event by using MAO inhibitors. In this context, reference is made to a publication by Toniello et al. [Biochim. Biophys. Acta 1765; pp 1-13 (2006)] reviewing the experimental evidences of the relationship between MAOI and the inhibition of cell apoptosis. Nevertheless, future investigations may show that MAOI offer biological activities presently unknown and not strictly related to MAO presence as, for example, suggested by De Marchi et al. [Biochem. Pharmacol. 66(9):17, pp 49-54 (2003)] for L-deprenyl.

The activity of Pargyline in the inhibition of MAO of type A and B has been reported by Malorni et al. [FEBS Lett. 426, pp 155-159 (1998)]. From the scientific work underlying the present invention it surprisingly results that Pargyline

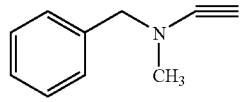

stimulates cell proliferation in the hair follicle, despite no similar indication resulted from official literature. It has been found that Pargyline shows the highest activity at a working concentration of about 0.01 mM to about 1 mM, preferably about 0.05 mM to about 0.1 mM. Of course, also at lower concentrations Pargyline shows some effects, but the results are usually less significant. Higher concentrations may work as well, but they usually do not lead to better results.

INDUSTRIAL APPLICATION

Pharmaceutical Applications

The core of the present invention concerns the use of Pargyline for the production of a medicament
for influencing the metabolism of hair follicles and the modulation of their vital cycle;
for treating disorders of hair follicles, in particular hair loss;
for treating diseases of hair growth; and
for treating skin diseases or disorders mediated by hair follicle metabolism.

The present invention also concerns a process for the cosmetic treatment of disorders of hair follicles, diseases of hair growth and skin diseases, or disorders mediated by hair follicle metabolism, which is characterised in that Pargyline is administered either by oral or topical application to hair or skin.

The administration of Pargyline can be topical or oral. In case of topical application, all kinds of compositions are possible: lotions, creams, emulsions and the like. For oral uptake, capsules are the preferred galenic forms. These embodiments are explained below in more detail.

Capsules and Microcapsules

For oral uptake, the encapsulation of the compositions represents a preferred embodiment. Usually, encapsulation can take place by using gelatine as a matrix. It is also possible to pre-pare capsules by adding a gelling agent such as, for example, alginate to the Pargyline composition and drop the mixture into a bath of a calcium salt. Both methods lead to macrocapsules having a diameter of about 1 cm to about 5 cm which are toxicologically safe and suitable for consumption.

It may also be desired to encapsulate Pargyline for the formulation of compositions which are developed for topical application. This can have different reasons: stabilisation against interaction with other compounds in the formulation, protection against chemical degradation, or simply for preparing a very aesthetical product. For this purpose, microcapsules are usually applied. "Microcapsules" are understood to be spherical aggregates with a diameter from about 0.1 to about 5 mm, which contain at least one solid or liquid core surrounded by at least one continuous membrane. More precisely, they are finely dispersed liquid or solid phases coated with film-forming polymers, during the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules there are also multiple-core aggregates, also known as microspheres, which contain two or more cores distributed in the continuous membrane material. In addition, single-core or multiple-core microcapsules may be surrounded by an additional second, third, etc. membrane. The membrane may consist of natural, semi-synthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are, inter alia, chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone. Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

Artificial Skin

Another object of the present invention refers to the use of Pargyline in the development of artificial skin. To date, the various models of artificial skin are obtained by producing the tissue "ex novo", starting from the isolation, amplification and culture of the various skin cell populations (i.e. keratinocytes, fibroblasts, melanocytes). Although the inclusion of hair follicles in the artificial skin tissue would greatly improve its biological efficiency, several technical obstacles in connection to the set-up of an appropriate culture medium impair the insertion of either the full organ or selected hair follicle cells population (e.g. derma papilla fibroblasts, outer root sheath keratinocytes, hair follicle melanocytes).

Usually, the possible approaches for tissue engineering in general and the use of artificial skin in particular fall into the following three categories:

Epidermal replacements—consisting of keratinocytes grown either alone (on the surface of a tissue culture flask), or in close association with a carrier vehicle, such as a polymeric film or bio-resorbable matrix.

Dermal replacements—consisting of a support structure, which is able to host the infiltration, adherence, proliferation and neo-matrix production by fibroblasts (and in some cases endothelial cells).

Skin substitutes—are a combination of the above, which are able to support both dermal and epidermal components.

At present two methods for the formation on artificial skin are well-established:

Mesh Scaffolding Method

According to the MS method, fibroblasts are transferred from the vials into roller bottles, which resemble liter soda bottles. The bottles are rotated on their sides for three to four weeks. The rolling action allows the circulation of oxygen, essential to the growth process. Subsequently the cells are removed from the roller bottles, combined with a nutrient-rich media, flowed through tubes into thin, cassette-like bioreactors housing the biodegradable mesh scaffolding, and sterilized with e-beam radiation. As the cells flow into the cassettes, they adhere to the mesh and begin to grow. The cells are flowed back and forth for three to four weeks. Each day, leftover cell suspension is removed and fresh nutrient is added Oxygen, pH, nutrient flow, and temperature are controlled by the culture system. As the new cells create a layer of dermal skin, the polymer disintegrates. Finally, when cell growth on the mesh is completed, the tissue is rinsed with more nutrient-rich media. A cryoprotectant is added. Cassettes are stored individually, labelled, and frozen.

Collagen Method

Using collagen as the raw material for making the artificial skin: in the first step cells are transferred to a culture system. A small amount of the cold collagen and nutrient media, approximately 12% of the combined solution, is added to the fibroblasts. The mixture is dispensed into molds and allowed to come to room temperature. As the collagen warms, it gels, trapping the fibroblasts and generating the growth of new skin cells. About two weeks after the collagen is added to the fibroblasts, the extracted keratinocytes are thawed and seeded onto the new dermal skin. They are allowed to grow for several days and then exposed to air, inducing the keratinocytes to form epidermal layers. Finally, the new skin is stored in sterile containers until needed.

The preparation of artificial skin containing hair follicles belongs to the state of the art; a suitable process is disclosed, for example, in the Chinese patent application CN 170523 A1. Although these technologies are presently providing some results on animal models only, it is clear that human hair follicle cultures included in artificial skin tissues could be achievable in a relatively short span of time. These new technologies will require the setting up of appropriate culture media, suitable to support the metabolic requirements of both artificial skin cells, hair follicle cells and/or the hair follicle. On this regards, the composition of these culture media would take great advantage from the addition of pargyline, in reason of its stimulant action on hair follicle metabolism and the modulatory effect on its cycle.

Cosmetic Compositions

Another object of the present invention is related to the use of Pargyline for the production of cosmetic compositions, in particular hair care compositions. Preferably, said cosmetic compositions comprise cosmetically acceptable carriers, which can be selected from water, aliphatic alcohols or polyols having 2 to 15 carbon atoms or oil bodies. The cosmetic compositions according to the present invention, preferably compositions for the treatment of human hair, may also contain additional compounds, such as, for example, surfactants, superfatting agents, pearlizing waxes, consistency factors, polymers, silicone compounds, waxes, stabilizers, antidandruff agents, biogenic agents, film formers, preservatives, perfume oils, dyes and the like as additional auxiliaries and additives.

Alcohols and Polyols

Ethanol, isopropyl alcohol or polyols, may be used as cosmetically acceptable carriers. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10 such as, for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines such as diethanolamine or 2-aminopropane-1,3-diol.

Oil Bodies

Suitable oil bodies forming cosmetically acceptable carriers are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons such as, for example, squalane, squalene or dialkylcyclohexanes, and/or mineral oils.

Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride(ether)sulfates, fatty acid amide (ether)sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl(ether)phosphates. If the anionic surfactants contain polyglycol ether chains, they may have a conventional homologue distribution although they preferably have a narrow-range homologue distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Emulsifiers

Other surfactants may also be added to the preparations as emulsifiers, including:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;
  addition products of 15 to 60 mol ethylene oxide onto castor oil and/or hydrogenated castor oil;
  polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
  addition products of 2 to 15 mol ethylene oxide onto castor oil and/or hydrogenated castor oil;
  partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example, cellulose);
  mono-, di and trialkyl phosphates and mono-, di- and/or tri-PEG-alkyl phosphates and salts thereof;
  wool wax alcohols;
  polysiloxane/polyalkyl polyether copolymers and corresponding derivatives;
  mixed esters of pentaerythritol, fatty acids, citric acid and fatty alcohol and/or mixed esters of $C_{6-22}$ fatty acids, methyl glucose and polyols, preferably glycerol or polyglycerol,
  polyalkylene glycols, and
  glycerol carbonate.

The addition products of ethylene oxide and/or propylene oxide onto fatty alcohols, fatty acids, alkylphenols, glycerol mono- and diesters and sorbitan mono- and diesters of fatty acids or onto castoroil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations.

Typical anionic emulsifiers are aliphatic $C_{12-22}$ fatty acids such as palmitic acid, stearic acid or behenic acid, for example, and $C_{12-22}$ dicarboxylic acids such as azelaic acid or sebacic acid, for example. Other suitable emulsifiers are zwitterionic surfactants. Zwitterionic surfactants are surface-active compounds, which contain at least one quaternary ammonium group and at least one carboxylate and one sulfonate group in the molecule. Particularly suitable zwitterionic surfactants are the so-called betaines such as the N-alkyl-N,N-dimethyl ammonium glycinates, for example cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Consistency Factors

The consistency factors mainly used are fatty alcohols or hydroxyfatty alcohols containing 12 to 22 carbon atoms, preferably 16 to 18 carbon atoms, and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used Thickening Agents Suitable thickeners are polymeric thickeners such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopolst [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat®, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol. Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Metal salts of fatty acids such as, for example, magnesium, aluminium and/or zinc stearate or ricinoleate may be used as stabilizers.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract, bambara nut extract, and vitamin complexes.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Piroctone Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, chamomile oil, clove oil, melissa oil, mint oil, cinnamon leaf oil, lime-blossom oil, juniper berry oil, vetiver oil, ohbanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

Usually the cosmetic compositions contain about 0.1 to about 15, preferably about 1 to about 10, and more preferably about 2 to about 5% by weight Pargyline, while the remaining part represents the carrier. The total percentage content of auxiliaries and additives may be from 1 to 50% by weight and is preferably from 5 to 40% by weight, based on the particular composition. The compositions may be produced by standard hot or cold processes.

EXAMPLES

Examples 1 to 3

Activity of MAOI on the Metabolism of Hair Follicles

Human anagen hair follicles were isolated from scalp skin and transferred for cultivation in sterile 24-well plates using a modified Williams' Medium E. Cultivation took place for nine days, while the experimental treatment of the follicles started 24 hours after the beginning of cultivation.

Hair follicles taken from a single donor were selected for the experiments after 18 h of cultivation Only follicles showing a good vital stage and a growth of not less than 0.2 mm were considered suitable to be maintained in culture. 4 groups comprising 9 follicles were prepared, plated at the density of three hair follicles/plate. The following experiments were conducted to demonstrate the activity of Pargyline on hair follicle growth in a concentration of 0.01 to 0.5 mM compared to a control group. The activity of the Pargyline treatment is demonstrated by the increase of growth of the hair follicles expressed in [mm] which was determined every two days. The growth of the hair follicles was studied by microphotography and subsequently determined by image analysis. All hair follicles were photographed every two days. The results are presented in Table 1:

TABLE 1

| | | Growth of hair follicles - elongation in [mm] ± standard error | | | | |
|---|---|---|---|---|---|---|
| | | Days of cultivation | | | | |
| Ex. | Sample | 1 | 3 | 5 | 7 | 9 |
| 0 | Control | 0 | 0.34 ± 0.04 | 0.73 ± 0.13 | 0.92 ± 0.18 | 1.05 ± 0.23 |
| 1 | Pargyline 0.01 mM | 0 | 0.51 ± 0.03 | 0.80 ± 0.07 | 1.11 ± 0.11 | 1.47 ± 0.15 |
| 2 | Pargyline 0.1 mM | 0 | 0.55 ± 0.04 | 0.91 ± 0.12 | 1.19 ± 0.17 | 1.60 ± 0.19 |

TABLE 1-continued

Growth of hair follicles - elongation in [mm] ± standard error

| | | Days of cultivation | | | | |
|---|---|---|---|---|---|---|
| Ex. | Sample | 1 | 3 | 5 | 7 | 9 |
| 3 | Pargyline 0.5 mM | 0 | 0.55 ± 0.05 | 0.81 ± 0.11 | 1.03 ± 0.14 | 1.17 ± 0.19 |

The results indicate that the addition of Pargyline leads to a significant increase in growth of the hair follicles.

Examples 4 to 6

Activity of Pargyline on the Decline of the Catagen Stage of Hair Follicles

The experiment according to Examples 1 to 3 was terminated after 9 days of cultivation. Subsequently, the hair follicles were subjected to a histological analysis by colouring with haematossilin and eosin in order to verify the morphological state of the dermopapilla. The results are shown in Table 2:

TABLE 2

Histological analysis of hair follicles

| Ex. | Sample | Anagen phase | Catagen phase |
|---|---|---|---|
| 0 | Control | 33% | 67% |
| 4 | Pargyline 0.01 mM | 78% | 22% |
| 5 | Pargyline 0.1 mM | 67% | 33% |
| 6 | Pargyline 0.5 mM | 56% | 44% |

The results indicate that the Pargyline treatment has significantly delayed the decline in the catagen phase of the hair follicles. Since growth of the hair follicles only takes place during the anagen phase, the results also support the stimulating effects of Pargyline.

Examples 7 and 8

Activity of Pargyline on the Number of Proliferative and Apoptotic Cells

After three days of cultivation, samples were taken in order to determine the relative number of cells being in the proliferative or apoptotic state. The cells in apoptotic state were determined using an Apoptag Fluorescein In-situ Apoptosis Detection Kit (Chemicon International cod. S7110), while those in the proliferative state were marked with the antibody Ki-67 (monoclonal mouse anti-human Ki-67, clone MIB1, Dako Cytomation cod. M7240). The total number of cells in the dermopapilla was analysed by marking their nuclei by means of DAPI (4',6-diamidino-2-phenylindol dihydrochloride). The percentage of cells in the proliferative or apoptotic state compared to the total number of cells was determined again by image analysis. The results are shown in Table 3.

TABLE 3

Number of cells in proliferative or apoptotic state ± standard error

| Ex. | Sample | Proliferative state | Apoptotic state |
|---|---|---|---|
| 0 | Control | 1.21% ± 0.3 | 0.69% ± 0.20 |
| 7 | Pargyline 0.01 mM | 1.67% ± 0.4 | 0.93% ± 0.37 |
| 8 | Pargyline 0.1 mM | 2.89% ± 0.99 | 0.95% ± 0.08 |

The results clearly indicate that the treatment of hair follicles with Pargyline significantly increases the number of cells in an active, proliferative state while it shows only a marginal effect in increasing the number of apoptotic cells.

Example 9

Comparative Examples C1 to C6

Activity of Pargyline Compared to Other MAOI

In order to show that the action of Pargyline on the metabolism of the hair follicles is novel and not reproducible by using other MAOIs, a comparative experiment has been performed according to the test methods as outlined in Examples 1 to 3. By comparing the results of Pargyline with the performances of either R- or S-Selegiline, we are in the position of concluding that no activity of the latter on alopecia, as disclosed in US 2004/0241220 A1, can be explained by adducing stimulant effects on hair follicle growth. The exclusive action of Pargyline is confirmed by the fact that also Chlorgyline did not exert any effect on hair growth. The results are compiled in Table 4.

TABLE 4

Growth of hair follicles - elongation in [mm] ± standard error

| | | Days of cultivation | | | | |
|---|---|---|---|---|---|---|
| Ex. | Sample | 1 | 3 | 5 | 7 | 9 |
| 0 | Control | 0 | 0.37 ± 0.02 | 0.52 ± 0.04 | 0.64 ± 0.13 | 0.81 ± 0.23 |
| 9 | Pargyline, 0.1 mM | 0 | 0.56 ± 0.02 | 0.78 ± 0.04 | 0.96 ± 0.05 | 1.22 ± 0.08 |
| C1 | R-Selegiline, 0.01 mM | 0 | 0.35 ± 0.02 | 0.52 ± 0.03 | 0.62 ± 0.05 | 0.80 ± 0.06 |
| C2 | R-Selegiline, 0.1 mM | 0 | 0.34 ± 0.02 | 0.53 ± 0.04 | 0.65 ± 0.06 | 0.82 ± 0.12 |
| C3 | S-Selegiline, 0.01 mM | 0 | 0.33 ± 0.02 | 0.49 ± 0.02 | 0.69 ± 0.03 | 0.84 ± 0.06 |

TABLE 4-continued

Growth of hair follicles - elongation in [mm] ± standard error

| | | Days of cultivation | | | | |
|---|---|---|---|---|---|---|
| Ex. | Sample | 1 | 3 | 5 | 7 | 9 |
| C4 | S-Selegiline, 0.1 mM | 0 | 0.35 ± 0.01 | 0.55 ± 0.02 | 0.70 ± 0.03 | 0.75 ± 0.06 |
| C5 | Chlorgyline, 0.01 mM | 0 | 0.35 ± 0.02 | 0.49 ± 0.02 | 0.61 ± 0.04 | 0.72 ± 0.07 |
| C6 | Chlorgyline, 0.1 mM | 0 | 0.33 ± 0.02 | 0.55 ± 0.04 | 0.67 ± 0.05 | 0.79 ± 0.09 |

The comparison clearly shows that Pargyline represents the only active species, while other MAOI—including the Selegiline isomers—show an activity comparable to the control, which means they do not show any effect at all.

The invention claimed is:

1. A method to fight hair loss and/or to promote hair growth, said method comprising orally administering an oral dosage form composition comprising an effective treating amount of pargyline as the sole pharmaceutical active ingredient to a mammal suffering from a disease associated with disorders of hair follicles and/or hair growth in order to increase the anagen period of the hair follicle cycle, retard its entry into the catagen phase, and increase the number of cells in the proliferative stage.

2. The method of claim 1 wherein pargyline is present in said oral dosage form composition in an amount of from about 0.1 to about 15% by weight based on the total weight of the composition.

3. A method to fight hair loss and/or to promote hair growth, said method comprising topically administering a topical dosage form composition comprising an effective treatment amount of pargyline and at least one cosmetically acceptable carrier to the hair or skin of a mammal suffering from a disease associated with disorders of hair follicles and/or hair growth in order to increase the anagen period of the hair follicle cycle, retard its entry into the catagen phase, and increase the number of cells in the proliferative stage.

4. The method of claim 3 wherein pargyline is present in said topical dosage form composition in an amount of from about 0.1 to about 15% by weight based on the total weight of the composition.

5. The method of claim 1 wherein said mammal is a human.

6. The method of claim 3 wherein said mammal is a human.

7. The method of claim 1 further including the step of adding alginate to the pargyline composition to provide a mixture and adding said mixture to a bath of a calcium salt to provide macrocapsules having a diameter of about 1 cm to about 5 cm.

8. The method of claim 3 further including the step of encapsulating the pargyline composition in microcapsules having a diameter of from about 0.1 to about 5 mm.

9. The method of claim 3 wherein the pargyline composition is a liquid and the method further includes the step of incorporating the liquid pargyline composition into a matrix to provide a microsponge which is thereafter coated with a film forming polymer.

10. The method of claim 3 further including the step of encapsulating the pargyline composition into microspheres containing two or more cores distributed in a continuous membrane material.

11. The method of claim 3 wherein the cosmetically acceptable carrier is selected from water, aliphatic alcohols, polyols having 2 to 15 atoms and oil bodies.

12. The method of claim 11 wherein the cosmetically acceptable carrier is ethanol or isopropanol.

13. The method of claim 11 wherein the cosmetically acceptable carrier is selected from the group consisting of glycerol, ethylene glycol, diethylene glycol, propylene glycol, butylene glycol, hexylene glycol, oligoglycerol mixtures with a degree of self-condensation of 1.5 to 10, trimethylol ethane, trimethylol propane, trimethylol butane, pentaerythritol, dipentaerythritol, methyl glucoside, butyl glucoside, sorbitol, mannitol, glucose, sucrose, glucamine, diethanolamine and 2-aminopropane-1,3-diol.

14. The method of claim 11 wherein the cosmetically acceptable carrier is selected from the group consisting of Guerbet alcohols based on fatty alcohols having 6 to 18 carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, esters of linear $C_6$-$C_{22}$-fatty acids with branched alcohols, esters of $C_{18}$-$C_{38}$-alkylhydroxy carboxylic acids with linear or branched $C_6$-$C_{22}$-fatty alcohols, esters of linear and/or branched fatty acids with polyhydric alcohols, and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, esters of $C_6$-$C_{22}$ fatty alcohols and/or Guerbet alcohols with benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, Guerbet carbonates based on fatty alcohols having 6 to 18 carbon atoms, esters of benzoic acid with linear and/or branched $C_6$-$C_{22}$-alcohols, linear or branched, symmetrical or asymmetrical dialkyl ethers having 6 to 22 carbon atoms per alkyl group, ring-opening products of epoxidized fatty acid esters with polyols, silicone oils and aliphatic or naphthenic hydrocarbons.

15. The method of claim 11 wherein the cosmetically acceptable carrier is selected from the group consisting of myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate, erucyl erucate, 2-ethylhexanol, dioctyl malate, propylene glycol, dimerdiol, trimertriol, dicaprylyl carbonate, dicaprylyl ether, cyclomethicones, squalene, dialkylcyclohexanes and mineral oil.

16. The method of claim 3 further including the step of adding a surfactant to the pargyline composition, the surfactant being selected from the group consisting of alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride(ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates, alkyl(ether)phosphates, alkylbetaines, alkylamidobetaines, aminopropionates, aminoglycinates, imidazolinium betaines and sulfobetaines.

17. The method of claim 3 further including the step of adding an emulsifier to the pargyline composition, the emulsifier being selected from the group consisting of
  products of the addition of 2 to 30 mol ethylene oxide and/or 0 to 5 mol propylene oxide onto linear $C_8$-$C_{22}$ fatty alcohols, products of the addition of 2 to 30 mol ethylene oxide and/or 0 to 5 mol propylene oxide onto $C_{12}$-$C_{22}$ fatty acids, products of the addition of 2 to 30 mol ethylene oxide and/or 0 to 5 mol propylene oxide onto alkyl phenols containing 8 to 15 carbon atoms in the alkyl group,
  $C_{12/18}$ fatty acid monoesters and diesters of addition products of 1 to 30 mol ethylene oxide onto glycerol,
  glycerol mono- and diesters and sorbitan mono- and diesters of saturated and unsaturated fatty acids containing 6 to 22 carbon atoms and ethylene oxide addition products thereof,
  addition products of 15 to 60 mol ethylene oxide onto castor oil and/or hydrogenated castor oil,
  polyglycerol polyricinoleate, polyglycerol poly-12-hydroxystearate, polyglycerol dimerate isostearate,
  addition products of 2 to 15 mol ethylene oxide onto castor oil and/or hydrogenated castor oil,
  partial esters based on linear, branched, unsaturated or saturated $C_{6/22}$ fatty acids, ricinoleic acid, or 12-hydroxystearic acid,
  partial esters based on glycerol, polyglycerol, pentaerythritol, dipentaerythritol, sorbitol, methyl glucoside, butyl glucoside, lauryl glucoside, or cellulose,
  mono-, di and trialkyl phosphates and mono-, di- and/or tri-PEG-alkyl phosphates and salts thereof,
  wool wax alcohols,
  polysiloxane/polyalkyl polyether copolymers and corresponding derivatives
  mixed esters of pentaerythritol, fatty acids, citric acid and fatty alcohol,
  mixed esters of $C_6$-$C_{22}$ fatty acids, methyl glucose, glycerol or polyglycerol,
  polyalkylene glycols and
  glycerol carbonate.

18. The method of claim 3 further including the step of adding an emulsifier to the pargyline composition, the emulsifier being selected from the group consisting of
  palmitic acid, stearic acid, behenic acid, azelaic acid, sebacic acid, cocoalkyl dimethyl ammonium glycinate, cocoacylaminopropyl dimethyl ammonium glycinate, cocoacylaminoethyl hydroxyethyl carboxymethyl glycinate, N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, alkylaminoacetic acids containing 8 to 18 carbon atoms in the alkyl group.

19. The method of claim 3 further including the step of adding a superfatting agent to the pargyline composition, the superfatting agent being selected from the group consisting of lanolin, lecithin, polyethoxylated or acylated lanolin, polyethoxylated or acylated lecithin derivatives, polyol fatty acid esters, monoglycerides and fatty acid alkanolamides.

20. The method of claim 3 further including the step of adding a consistency factor to the pargyline composition, the consistency factor being selected from the group consisting of fatty alcohols or hydroxyfatty alcohols containing 12 to 22 carbon atoms, partial glycerides, fatty acids and hydroxyfatty acids.

21. The method of claim 3 further including the step of adding a thickening agent to the pargyline composition, the thickening agent being selected from the group consisting of hydrophilic silicas, xanthan gum, guar-guar, agar-agar, alginates and tyloses, carboxymethyl cellulose, hydroxyethyl cellulose, high molecular weight polyethylene glycol monoesters and diesters of fatty acids, polyacrylates, polyacrylamides, polyvinyl alcohol, polyvinyl pyrrolidone, ethoxylated fatty acid glycerides, pentaerythritol, trimethylol propane, sodium chloride and ammonium chloride.

22. The method of claim 3 further including the step of adding a polymer to the pargyline composition, the polymer being selected from the group consisting of quaternized hydroxyethyl cellulose, cationic starch, copolymers of diallyl ammonium salts and acrylamides, quaternized vinyl pyrrolidone/vinyl imidazole polymers, condensation products of polyglycols and amines, quaternized collagen polypeptides, quaternized wheat polypeptides, polyethyleneimine, cationic silicone polymers, copolymers of adipic acid and dimethylaminohydroxypropyl diethylenetriamine, copolymers of acrylic acid with dimethyl diallyl ammonium chloride, polyaminopolyamides, cationic chitin derivatives, condensation products of dihaloalkyls, cationic guar gum, quaternized ammonium salt polymers, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers, derivatized cellulose ethers and silicones.

23. The method of claim 3 further including the step of adding a pearlizing wax to the pargyline composition, the pearlizing wax being selected from the group consisting of ethylene glycol distearate, cocofatty acid diethanolamide, stearic acid monoglyceride, long-chain esters of tartaric acid, fatty alcohols, fatty ketones, fatty aldehydes, fatty ethers, fatty carbonates which contain in all at least 24 carbon atoms, stearic acid, hydroxystearic acid, behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

24. The method of claim 3 further including the step of adding a silicone to the pargyline composition, the silicone being selected from the group consisting of dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds, and simethicones.

25. The method of claim 3 further including the step of adding a wax to the pargyline composition, the wax being selected from the group consisting of candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes, montan ester waxes, sasol waxes, hydrogenated jojoba waxes, polyalkylene waxes, polyethylene and glycol waxes.

26. The method of claim 3 further including the step of adding a stabilizer to the pargyline composition, the stabilizer being selected from the group consisting of magnesium stearate, aluminium stearate, zinc stearate, magnesium ricinoleate, aluminum ricinolate and zinc ricinolate.

27. The method of claim 3 further including the step of adding a perfume oil to the pargyline composition, the perfume oil being selected from the group consisting of the extracts of blossoms, extracts of stems, extracts of leaves, extracts of fruits, extracts of fruit peel, extracts of roots, extracts of woods, extracts of herbs and grasses, extracts of needles and branches, resins, balsams, perfume oils derived from animals, benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate, citral, citronellal, citronellyloxyacetaldehyde, cyclamen aldehyde, hydroxycitronellal, lilial and bourgeonal, ionones, isomethylionone and methyl cedryl ketone, anethol, citronellol, eugenol, isoeugenol, geraniol, linalool, phenylethyl alcohol and terpineol.

28. The method of claim 3 further including the step of adding a perfume oil to the pargyline composition, the perfume oil being selected from the group consisting of sage oil, chamomile oil, clove oil, melissa oil, mint oil, cinnamon leaf oil, lime-blossom oil, juniper berry oil, vetiver oil, ohbanum oil, galbanum oil, ladanum oil, bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

29. The method of claim 3 further including the step of adding a dye to the pargyline composition, the dye being selected from the group consisting of cochineal red A, patent blue V, indigotin, chlorophyllin, quinoline yellow, titanium dioxide, indanthrene blue RS, madder lake and luminol.

* * * * *